(12) United States Patent
Wang et al.

(10) Patent No.: US 12,102,647 B2
(45) Date of Patent: Oct. 1, 2024

(54) CITRINE PLEUROTUS POLYSACCHARIDE AND APPLICATIONS THEREOF

(71) Applicant: Qi Wang, Changchun (CN)

(72) Inventors: Qi Wang, Changchun (CN); Ling Su, Changchun (CN); Jintao Yang, Changchun (CN)

(73) Assignee: Qi Wang, Changchun (CN)

( * ) Notice: Subject to any disclaimer, the term of this patent is extended or adjusted under 35 U.S.C. 154(b) by 153 days.

(21) Appl. No.: 17/564,777

(22) Filed: Dec. 29, 2021

(65) Prior Publication Data

US 2023/0099458 A1    Mar. 30, 2023

(30) Foreign Application Priority Data

Sep. 29, 2021   (CN) .......................... 202111153946.8

(51) Int. Cl.
*A61K 31/7004* (2006.01)
*A61K 31/715* (2006.01)
*A61P 21/00* (2006.01)

(52) U.S. Cl.
CPC ........ *A61K 31/7004* (2013.01); *A61K 31/715* (2013.01); *A61P 21/00* (2018.01)

(58) Field of Classification Search
CPC .. A61K 31/715; A61K 31/7004; A61K 31/70; A61P 21/00; C08L 5/00; C08B 37/006; C08B 37/0003
See application file for complete search history.

(56) References Cited

PUBLICATIONS

Oxford English Dictionary definition of "polysaccharide", accessed Dec. 27, 2023. (Year: 2023).*

Wang, J.-C.; et al. "Antigenotoxicity of extracts from Pleurotus citrinopileatus" 2005, Journal of the Science of Food and Agriculture, vol. 85, pp. 770-778. (Year: 2005).*

Wang, Q.; et al. "Structural characterization of a novel polysaccharide from Pleurotus citrinopileatus and its antitumor activity on H22 tumor-bearing mice" 2021, Int. J. of Biological Macromolecules, vol. 168, pp. 251-260. (available online Dec. 9, 2020) (Year: 2020).*

Zhang, J. et al. "Antitumor Polysaccharides from a Chinese Mushroom, "Yuhuangmo," the Fruiting Body of Pleurotus citrinopileatus" 1994, Biosci. Biotech. Biochem., vol. 58, pp. 1195-1201. (Year: 1994).*

Wu, C.-Y.; et al. "Effect of Carbon and Nitrogen Sources on the Production and Carbohydrate Composition of Exopolysaccharide by Submerged Culture of Pleurotus citrinopileatus" 2008, J. Food Drug Analysis, vol. 16, pp. 61-67. (Year: 2008).*

* cited by examiner

*Primary Examiner* — Eric Olson
*Assistant Examiner* — Benjamin M Brandsen

(57) ABSTRACT

A citrine pleurotus (*Pleurotus citrinopileatus*) polysaccharide and application thereof are provided, which relate to the field of natural product development and utilization. The citrine pleurotus polysaccharide includes xylose, glucose, galactose, glucuronic acid, fucose, fructose and arabinose. The citrine pleurotus polysaccharide can be applied in preparing drugs for treating sarcopenia caused by cancers. It is demonstrated that the polysaccharide of citrine pleurotus may increase a body weight and a spleen weight, restore morphology, number and density of muscle fibers, reduce inflammatory response and decrease expressions of signature proteins of Atrogin-1 and MuRF-1 for sarcopenia, and alleviate symptoms of tumor-induced sarcopenia in mice with colon cancer cachexia. New effects of polysaccharides of citrine pleurotus are discovered, which provides new ideas for exploitating the citrine pleurotus and treating the sarcopenia caused by cancers.

2 Claims, 7 Drawing Sheets

Specification includes a Sequence Listing.

Note: *P<0.05, **P<0.01 compared with the normal group; compared with the model group, △P<0.05, △△P<0.01.

US 12,102,647 B2

CITRINE PLEUROTUS POLYSACCHARIDE AND APPLICATIONS THEREOF

TECHNICAL FIELD

The disclosure relates to the field of development and utilization of natural products, in particular to a citrine pleurotus (*Pleurotus citrinopileatus*) polysaccharide and applications thereof.

BACKGROUND

50%-80% of cancer patients suffer from sarcopenia, which is characterized by inflammatory reaction, involving multiple organ syndromes, and has various, devastating and irreversible effects on the body. Sarcopenia seriously affects the quality of life of patients and even could be fatal. In 2016, sarcopenia was listed as a degenerative disease by the World Health Organization together with neurological diseases such as Alzheimer's disease and Parkinson's disease. However, at present, there is no effective anti-tumor medicine for sarcopenia.

Citrine pleurotus, also known as *Pleurotus citrinopileatus*, belongs to *Basidiomycotina, Laminaria, Agaricus, Pleurotus*, which is distributed in the north of temperate zone in the northern hemisphere, as well as in three northeastern provinces of China, Hebei, Hunan, Sichuan and Tibet. The fruiting body of citrine pleurotus is delicious, with rich nutrition, sweet taste and warm nature. Citrine pleurotus may be absorbed by the spleen and lung meridian, the mushroom has the effects of nourishing and strengthening, moistening the lungs, generating fluid and stopping dysentery, and has biological activities such as reducing blood lipid, antioxidation and improving body immunity. However, citrine pleurotus' bioactivity, active ingredients and preparation methods for alleviating tumor induced sarcopenia have not been reported.

SUMMARY

A purpose of the disclosure is to provide a citrine pleurotus polysaccharide and applications thereof, so as to solve the problems existing in the prior art and improve the sarcopenia caused by tumor.

In order to achieve the above purpose, the disclosure provides the following schemes:

One of the technical schemes of the disclosure is a citrine pleurotus polysaccharide, which includes xylose, glucose, galactose, glucuronic acid, fucose, fructose and arabinose.

Further, the citrine *pleurotus* polysaccharide comprising xylose, glucose, galactose, glucuronic acid, fucose, fructose and arabinose.

Further, the xylose accounts for more than 50% in molar percentage of the polysaccharide of citrine pleurotus.

Further, the glucose accounts for more than 15% in molar percentage of the polysaccharide of citrine pleurotus.

Further, the galactose accounts for more than 4% in molar percentage of the polysaccharide of citrine pleurotus.

Further, the glucuronic acid accounts for more than 1% in molar percentage of the polysaccharide of citrine pleurotus.

Further, each of the fucose, fructose and arabinose accounts for less than 3% in molar percentage of the polysaccharide of citrine pleurotus.

Further, a molecular weight of a neutral homogeneous component polysaccharide in the citrine pleurotus polysaccharide is $3.00 \times 10^5$-$1.00 \times 10^6$ Da (Dalton), and a molecular weight of an acidic homogeneous component polysaccharide is $1.20 \times 10^5$-$3.50 \times 10^5$ Da.

A second technical scheme of the disclosure relates to the application of the citrine pleurotus polysaccharide in the preparation of drugs for treating sarcopenia.

Further, the sarcopenia is caused by a cancer.

Further, the cancers is colon cancer, stomach cancer, lung cancer, liver cancer, pancreatic cancer, colorectal cancer, esophageal cancer, lymphoma or breast cancer.

A third technical scheme of the disclosure relates to a drug/medicine for treating sarcopenia, which includes the citrine pleurotus polysaccharide mentioned above and medically acceptable excipients.

The disclosure can achieve the following technical effects:

The present disclosure demonstrates that the polysaccharide of citrine pleurotus may increase the body weight and spleen weight, restore the morphology, number and density of muscle fibers, reduce the inflammatory response and decrease the expression of the signature proteins of sarcopenia, Atrogin-1 and MuRF-1, and alleviate the symptoms of tumor-induced sarcopenia in mice with colon cancer cachexia.

The present disclosure has discovered new effects of polysaccharides of citrine pleurotus, which provides new ideas for the exploitation of citrine pleurotus and the treatment of sarcopenia caused by cancer.

BRIEF DESCRIPTION OF DRAWINGS

In order to more clearly explain the embodiments of the present disclosure or the technical solutions in the prior art, the following will briefly introduce the drawings needed in the embodiments. Obviously, the drawings in the following description are only some embodiments of the present disclosure, and for ordinary technicians in the field, other drawings may be obtained according to these drawings without creative efforts.

DETAILED DESCRIPTION OF EMBODIMENTS

Figure 1:
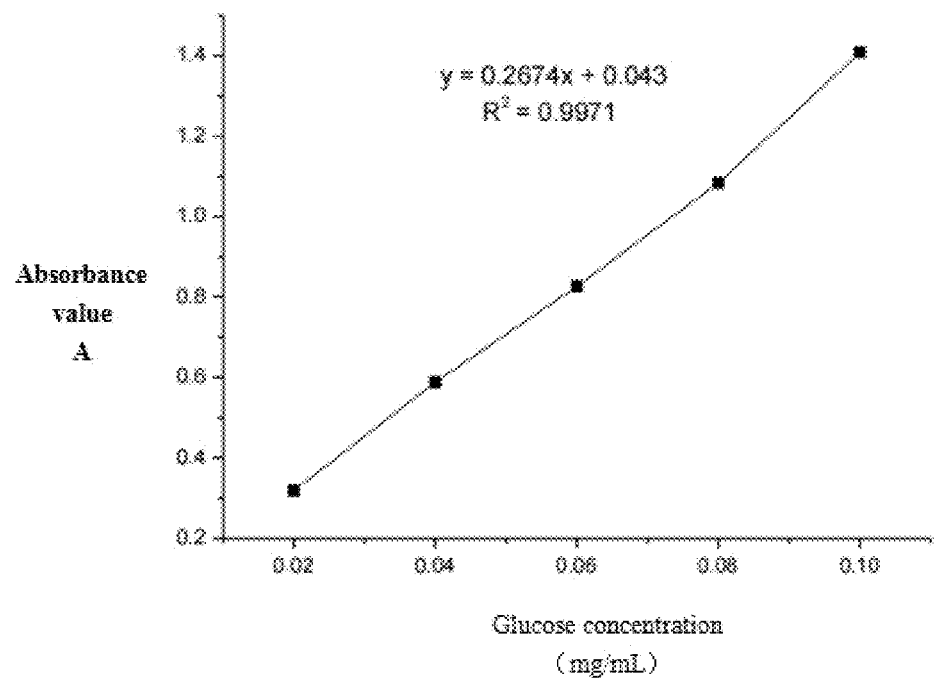
FIG. 1 shows a standard curve of glucose content in polysaccharide of citrine pleurotus prepared in Embodiment 1.

Now, various exemplary embodiments of the present disclosure will be described in detail. This detailed description should not be considered as a limitation of the present disclosure, but should be understood as a more detailed description of some aspects, characteristics and embodiments of the present disclosure.

It should be understood that the terms used in this disclosure are only for describing specific embodiments, and are not used to limit the disclosure. In addition, for the numerical range in the present disclosure, it should be understood that each intermediate value between the upper limit and the lower limit of the range is also specifically disclosed. Any stated value or intermediate value within the stated range and any other stated value or every smaller range between intermediate values within the stated range are also included in the present disclosure. The upper and lower limits of these smaller ranges may be independently included or excluded from the range.

Unless otherwise specified, all technical and scientific terms used herein have the same meaning as commonly understood by the ordinary technicians in the field of this disclosure. Although the present disclosure only describes the preferred methods and materials, any methods and materials similar or equivalent to those described herein may also be used in the practice or testing of the present disclosure. All documents mentioned in this specification are incorporated by reference to disclose and describe the methods and/or materials related to the documents. In case of conflict with any incorporated documents, the contents of this specification shall prevail.

Without departing from the scope or spirit of the present disclosure, it is obvious to those skilled in the art that many modifications and changes may be made to the specific embodiments of the present disclosure. Other embodiments obtained from the description of the present disclosure will be obvious to the skilled person. The description and embodiment of that present disclosure are exemplary only.

The terms "includes", "comprise", "has", "contains", etc. used in this paper are open-ended terms, i.e., meaning including but not limited to.

Unless otherwise specified, the room temperature in the embodiment of the disclosure refers to 20-25° C.

Embodiment 1

S1: putting the fruiting body of citrine pleurotus and deionized water into a high speed blender according to the mass ratio of 1:40, breaking cell walls and extracting for 8 min under the power of 1200 W to obtain the supernatant; at room temperature, concentrating the supernatant to 20% of the original under reduced pressure, and then carrying out alcohol precipitation with ethanol with 4 times the volume and 80% volume fraction of the concentrated solution to obtain the crude polysaccharide solution of citrine pleurotus;

S2: adding ¼ volume of Sevage solution (chloroform:n-butanol=4:1 by volume ratio) to the crude polysaccharide solution of citrine pleurotus, and fully stirring it with a magnetic stirrer for 1 h (the function of Sevage solution is to remove the protein in the polysaccharide solution); after static stratification, collecting the upper polysaccharide solution, repeating the operation for 3 times until there is no denatured protein between the upper and lower layers, and volatilizing the organic reagent to obtain citrine pleurotus polysaccharide.

Embodiment 2

S1: putting the fruiting body of citrine pleurotus and deionized water into a beaker according to the mass ratio of 1:50, and obtaining the supernatant after water bath at 90° C. for 40 min; carrying out centrifugal separation, repeating the precipitation extraction twice, concentrating the supernatant to 20% of the original under reduced pressure, and then carrying out alcohol precipitation with ethanol with 4 times the volume and 80% volume fraction of the concentrated solution to obtain the crude polysaccharide solution of citrine pleurotus;

S2: adding ¼ volume of Sevage solution (chloroform:n-butanol=4:1 by volume ratio) to the crude polysaccharide solution of citrine pleurotus, and fully stirring it with a magnetic stirrer for 1 h (the function of Sevage solution is to remove the protein in the polysaccharide solution); after static stratification, collecting the upper polysaccharide solution, repeating the operation for 3 times until there is no denatured protein between the upper and lower layers, and volatilizing the organic reagent to obtain citrine pleurotus polysaccharide.

Embodiment 3

S1: putting the fruiting body of citrine pleurotus and deionized water into a beaker according to the mass ratio of 1:40, and conducting ultrasonic treatment at 500 W for 16 min, followed by water bath at 90° C. for 2 h.; concentrating the supernatant to 20% of the original under reduced pressure, and then carrying out alcohol precipitation with ethanol with 4 times the volume and 80% volume fraction of the concentrated solution to obtain the crude polysaccharide solution of citrine pleurotus;

S2: adding ¼ volume of Sevage solution (chloroform:n-butanol=4:1 by volume ratio) to the crude polysaccharide solution of citrine pleurotus, and fully stirring it with a magnetic stirrer for 1 h (the function of Sevage solution is to remove the protein in the polysaccharide solution); after static stratification, collecting the upper polysaccharide solution, repeating the operation for 3 times until there is no denatured protein between the upper and lower layers, and volatilizing the organic reagent to obtain citrine pleurotus polysaccharide.

Figure 2:
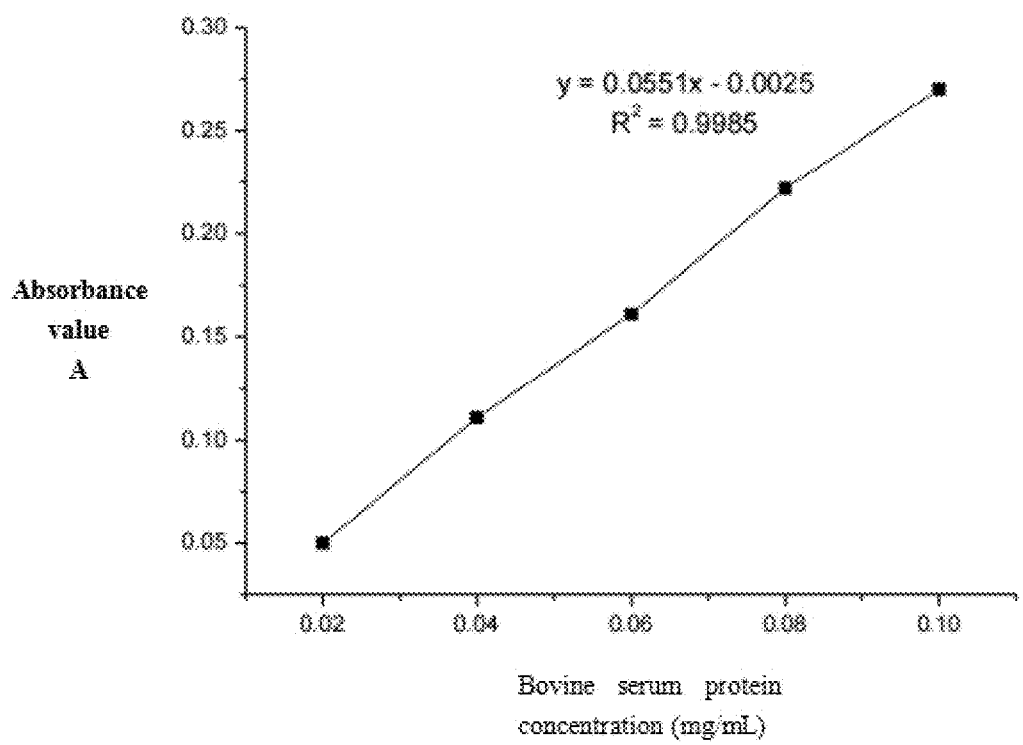
FIG. 2 shows a standard curve of protein content in polysaccharide of citrine pleurotus made in Embodiment 1.
Figure 12:
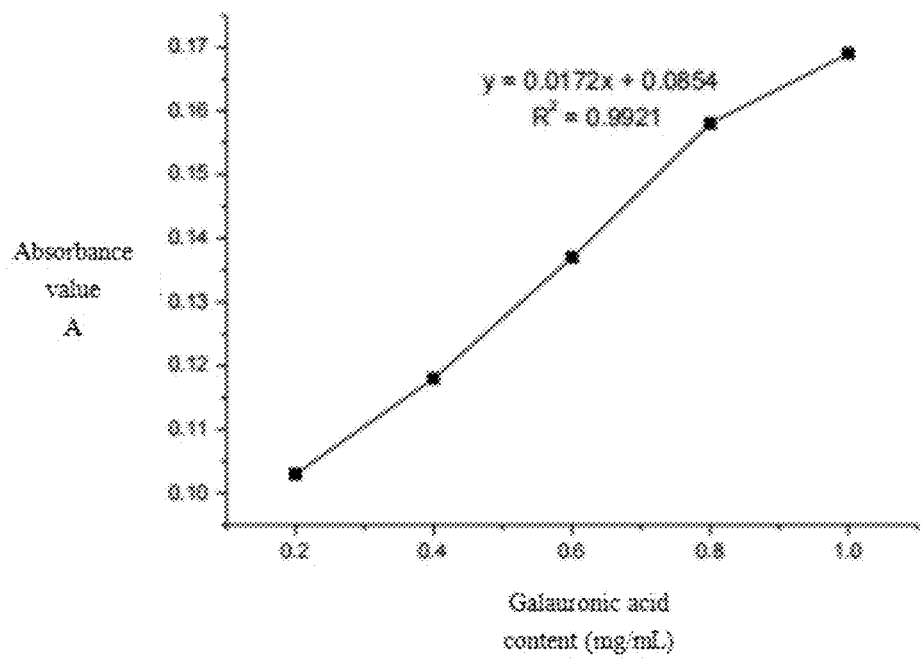
FIG. 12 shows a standard curve of galauronic acid content in the polysaccharides of of citrine pleurotus prepared in Embodiment 1.

Test Embodiment 1: Detecting the Active Ingredient of Citrine Pleurotus Polysaccharide Prepared in Embodiment 1 and the Muscle Attenuation Effect Thereby on Colon Cancer Cachexia Mice 1. Determination of Ingredients in Polysaccharide of Citrine Pleurotus Detecting the sugar content in citrine pleurotus by phenol sulfuric acid method. The standard curve of glucose content in citrine pleurotus polysaccharide is shown in FIG. 1; using Coomassie brilliant blue G250 method to detect the protein content in citrine pleurotus. The standard curve of protein content is shown in FIG. 2; using m-hydroxybiphenyl method to determine the uronic acid content of citrine pleurotus polysaccharide. The standard curve of uronic acid content is shown in FIG. 12. It can be seen from FIG. 1, FIG. 2 and FIG. 12 that the sugar content, protein content and uronic acid content of citrine pleurotus polysaccharide prepared in Embodiment 1 are 51.09%, 9.87% and 1.24% respectively.

2. Determination of Molecular Weight of Polysaccharide from Citrine Pleurotus

Determining the molecular weight of polysaccharides in citrine pleurotus by high performance gel permeation chromatography. Determining the molecular weight of the samples according to the retention time of the samples. The smaller the retention time, the greater the molecular weight. The chromatographic conditions are RID-10A parallax refractive detector and TSK-gel G-3000PWXL chromatographic column (7.8×300 nm), the mobile phase is distilled water, the flow rate is 0.6 mL/min, the column temperature is 35° C., and the injection volume is 10 μL.

Figure 3:
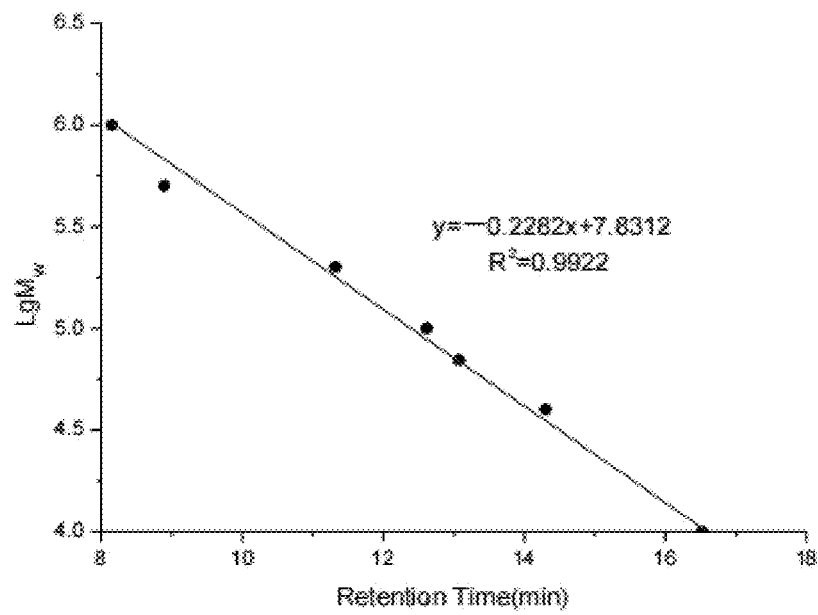
FIG. 3 illustrates a standard curve of molecular weight of standard dextran.
Figure 4:
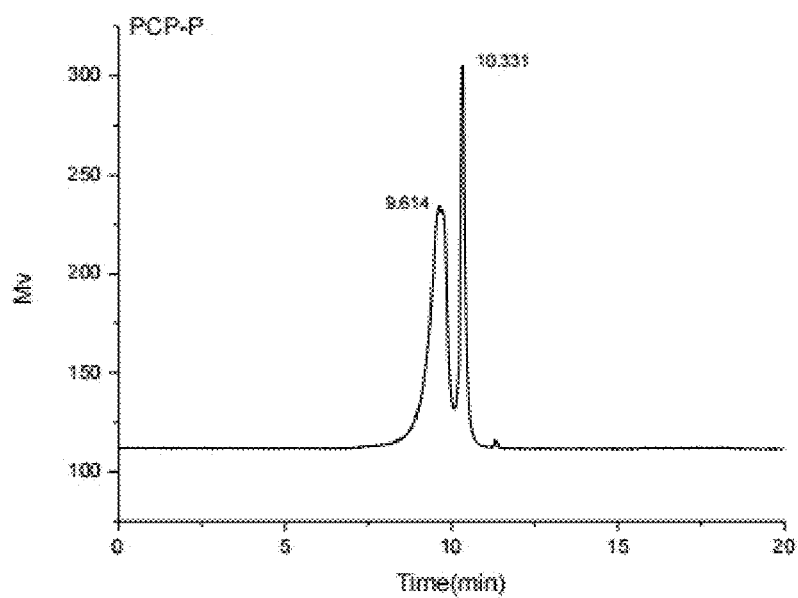
FIG. 4 shows a high performance gel permeation chromatogram of polysaccharide of citrine pleurotus prepared in Embodiment 1.

The molecular weight standard curve of dextran is shown in FIG. 3, and the equation of molecular weight standard curve is $y=-0.2282x+7.8312$, $R^2=0.9922$. FIG. 4 illustrates the high performance gel permeation chromatogram of citrine pleurotus polysaccharide. According to the retention time and standard curve, the molecular weight of neutral homogeneous polysaccharide and acidic homogeneous polysaccharide in citrine pleurotus polysaccharide is $3.00\times10^5$-$1.00\times10^6$ Da and $1.20\times10^5$-$3.50\times10^5$ Da, with a ratio of 18.3:1.

3. Analysis of Monosaccharide Composition of Polysaccharide from Citrine Pleurotus:

Weighing 5 mg of citrine pleurotus polysaccharide sample prepared in Embodiment 1, adding the configured 5% TFA acid solution (trifluoroacetic acid), heating at 121° C. for 2 h; blowing dry with nitrogen, adding methanol for cleaning and then blowing dry, and repeating the above step for 3 times. Adding sterile water to dissolve and transfer the sample into a clean chromatographic bottle for testing. Setting mobile phase: phase A: $ddH_2O$; Phase B: 200 mM NaOH; phase C: 200 mM NaOH/500 mM NaAC; flow rate: 0.5 mL/min.

Figure 5:
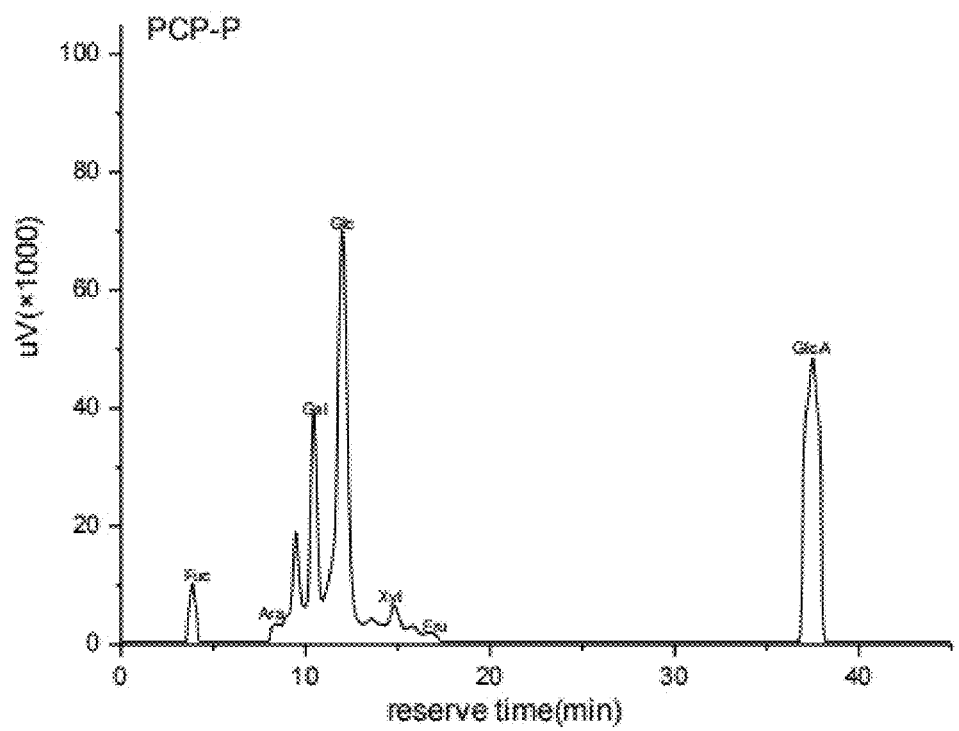
FIG. 5 illustrates a HPLC graph of monosaccharide compositions of the polysaccharide of citrine pleurotus prepared in Embodiment 1.

The monosaccharide composition HPLC of citrine pleurotus polysaccharide is shown in FIG. 5. It can be seen from FIG. 5 that the citrine pleurotus polysaccharide prepared in Embodiment 1 includes xylose, glucose, galactose, glucuronic acid, fucose, fructose and arabinose, and the molar ratio is 60.905:26.281:7.754:3.803:0.697:0.418:0.139.

4. Infrared Spectrum Analysis of Polysaccharide from Citrine Pleurotus

Figure 6:
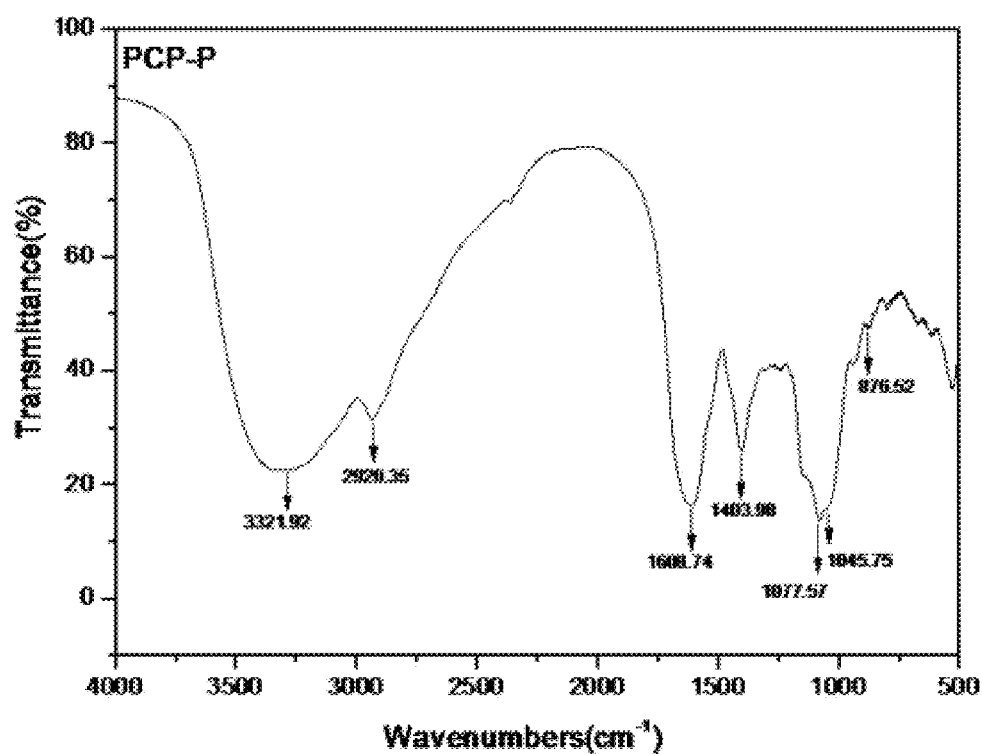
FIG. 6 shows an infrared (IR) spectra of the polysaccharides of citrine pleurotus prepared in Embodiment 1.

Weighing 1.5 mg of citrine pleurotus polysaccharide prepared in Embodiment 1 and fully mixing the product with 200 mg of chromatographic pure KBr, grinding with agate mortar and pressing, and taking 200 mg KBr as the background. Carrying out the infrared spectrum scanning analysis is carried out with an infrared spectrometer in the range of 4000-500 $cm^{-1}$. The result is shown in FIG. 6. It can be known from FIG. 6 that the polysaccharide prepared in embodiment 1 is β-furanose.

5. Anti-Muscle Attenuation Effect of Citrine Pleurotus Polysaccharide in Mice with Colon Cancer Cachexia
5.1 Animal Experiment Design and Treatment
5.1.1 Animal Grouping Randomly dividing BALB/c mice after adaptive feeding for one week into normal group, colon cancer cachexia model group, citrine pleurotus polysaccharide low-dose group, citrine pleurotus polysaccharide medium-dose group, citrine pleurotus polysaccharide high-dose group and Sijunzi granule (with main ingredients of *Codonopsis pilosula*, fried *atractylodes, Poria cocos* and *Radix Glycyrrhizae* Preparata.) positive control group, with 10 mice in each group.

5.1.2 Treatment of Cells and Establishment of Tumor Mouse Model

Culturing Mice CT26 colon cancer cells normally in DMEM medium containing 10% fetal bovine serum and 1% penicillin-streptomycin double antibody, adjusting with phosphate buffer, and the density of collected cells is $2\times10^8$/mL for modeling in vivo. Except the normal group, injecting the other five groups of mice subcutaneously with CT26 cells $1\times10^7$ (dissolved in 0.1 mL PBS+0.1 mL basement glue) on the right back, and observing the tumor growth, and starting the experiment after 7 days.

5.1.3 Intervention of Administration

Starting gavage after 7 days when the tumor is observed. In the normal and model groups, mice are gavaged with 0.2 mL of physiological saline each; in the polysaccharide administration group, polysaccharide is dissolved in physiological saline and gavaged at 0.2 mL/each, and the doses are 200 mg/kg, 400 mg/kg and 600 mg/kg, respectively; (Positive group with Sijunzi granule group) is converted to 2250 mg/kg based on the daily dose for adults, dissolved in saline and gavaged at 0.2 mL/only. The dose is determined to be safe and without toxic side effects in all groups. During this period, all mice are free to eat and drink water. The weight of mice is weighed every two days, the condition of mice is observed, and the eating and drinking conditions are recorded. The experimental administration lasts for 14 days.

5.1.4 Animal Treatment and Sample Collection

After weighing all the mice's weight on 14th day, the orbital blood is taken and dissected. The collected whole blood of mice is collected in a sterile RNase-free tube and centrifuged twice (3500 rpm/min) at 4° C. for 10 min each time, and the supernatant is collected. The serum is stored in an ultra-low temperature refrigerator at −80° C. until detection. Part of the dissected heart, lung, liver, kidney, spleen and gastrocnemius muscle is fixed in 10% neutral formalin buffer, and the other part is quickly frozen in liquid nitrogen after being put into sterile RNase-free tubes, and also kept at −80° C. for use. Feces are carefully collected from the large intestine of mice, stored in sterile RNase-free tubes, then quickly frozen with liquid nitrogen, and also stored at −80° C. for use.

Results: after dissecting the mice, comparing the weight of the mice's net body, gastrocnemius muscle and tumor. The weight of the mice is shown in FIG. 7, and the weight of gastrocnemius muscle and tumor is shown in TABLE 1:

TABLE 1

| Group | Gastrocnemius muscle | Tumour |
|---|---|---|
| Normal group | 0.132 ± 0.019<sup>Δ</sup> | — |
| Model group | 0.092 ± 0.021* | 4.157 ± 1.637 |
| Low dose group | 0.094 ± 0.016* | 3.461 ± 1.039 |
| Medium dose group | 0.1034 ± 0.026 | 3.360 ± 1.343 |
| High dose group | 0.112 ± 0.017 | 2.611 ± 1.161 |
| Positive drug group | 0.121 ± 0.021 | 3.081 ± 1.665 |

Figure 7A:
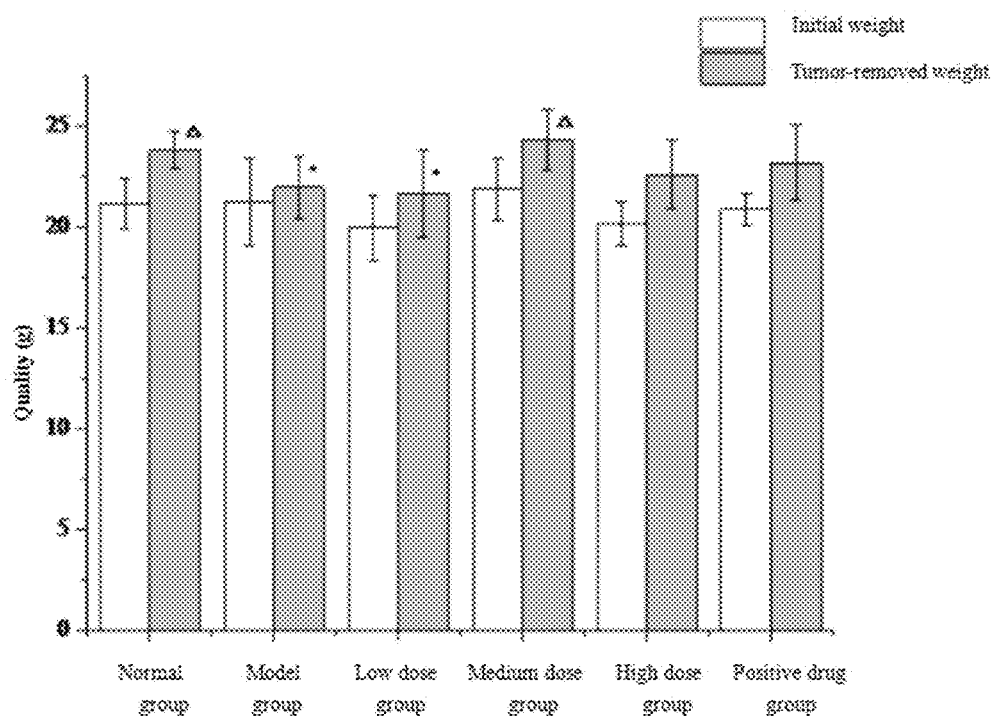
FIG. 7A and FIG. 7B show weights of mice in Embodiment 1.
Figure 7B:
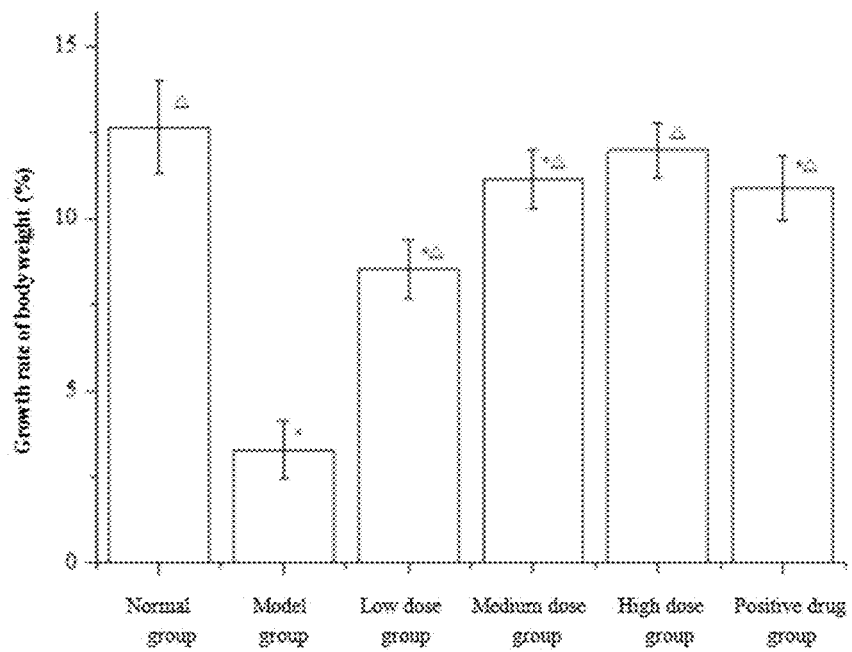

From FIG. 7 and TABLE 1, it can be known that citrine pleurotus polysaccharide may increase the weight and gastrocnemius muscle mass of mice with muscular dystrophy caused by colon cancer, and inhibit tumor growth.

Figure 8:
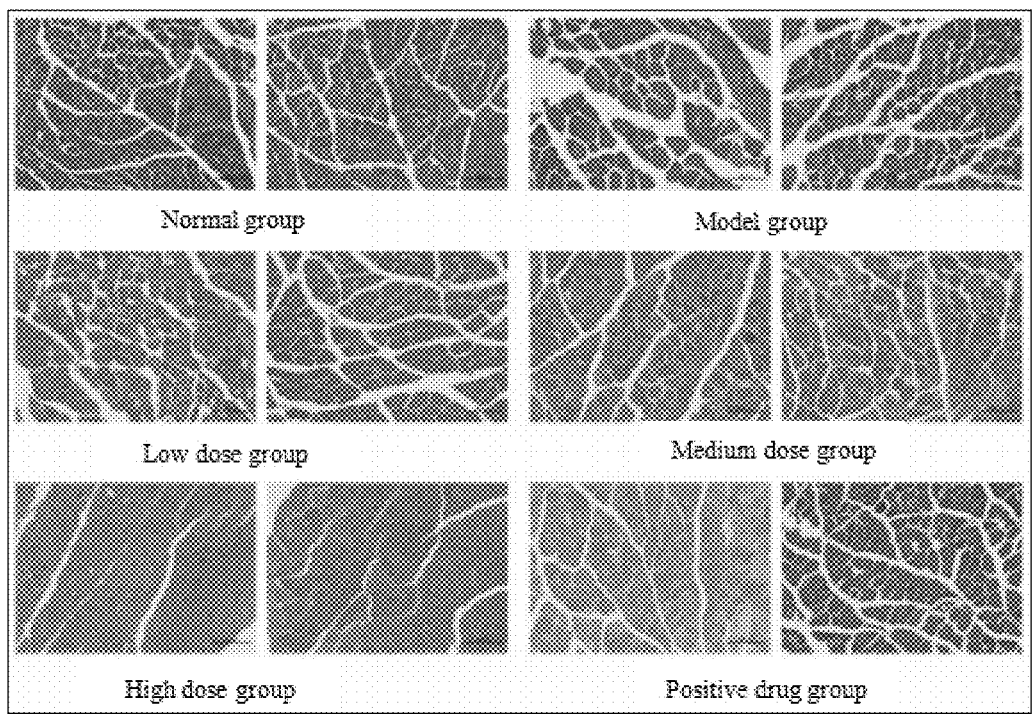
FIG. 8 shows effects of histomorphology of mice gastrocnemius muscle in Embodiment 1.

5.2 Hematoxylin-Eosin Staining of Gastrocnemius Muscle and Detection of Some Indexes Dehydrating the gastrocnemius muscle tissue block fixed with paraformaldehyde in ethanol solution according to the gradient from low concentration to high concentration, and transparent with xylene, absolute ethanol and pure xylene. Putting the transparent tissue block into the mixed solution of paraffin and xylene with equal volume for 15 min, and then put into pure paraffin for 20-30 min to embed the tissue block. Cutting the embedded tissue wax block into thin slices according to the required slice thickness, sticking the slices on the glass slide, and putting the glass slide in a constant temperature box for drying. The slices are dewaxed by xylene twice, put into gradient ethanol from high concentration to low concentration for 3-5 min, then put into distilled water for 3 min, dyed with hematoxylin dye solution and eosin dye solution, washed away the excess red with 95% ethanol, and then put into absolute ethanol for 3-5 min. The slices are put into the mixture of ethanol and xylene with equal volume for 5 min, then put into pure xylene for transparency twice, and finally sealed with neutral gum. Placing the slide under the microscope, and using Eclipse Ci-L photographic microscope to select the target area of the tissue for 200 times imaging. When imaging, trying to fill the whole field of vision with the tissue to ensure that the background light of each photo is consistent. After imaging, useing Image-Pro Plus 6.0 analysis software to count the number of muscle fibers and the corresponding total area of muscle fibers in each drawing, and calculating the single muscle fiber area=total area of muscle fibers/number of muscle fibers, muscle fiber density=number of muscle fibers/visual field area. The influence of pathomorphology (HE, ×400) of mouse gastrocnemius muscle tissue is shown in FIG. 8, and the number, area and density of mouse muscle fibers are shown in TABLE 2:

Adding 100 μL of enzyme standard reagent and placing the plate with sealing film at 37° C. for 60 min After the incubation, discarding the liquid and washing each well repeatedly with diluted washing solution and finally patting dry. Adding 50 μL of color developer A and B to each well, shaking well, and then adding 50 μL of termination solution to terminate the reaction after 15 min of color development at 37° C. The absorbance values of each well are measured at 450 nm in sequence.

Figure 9A:
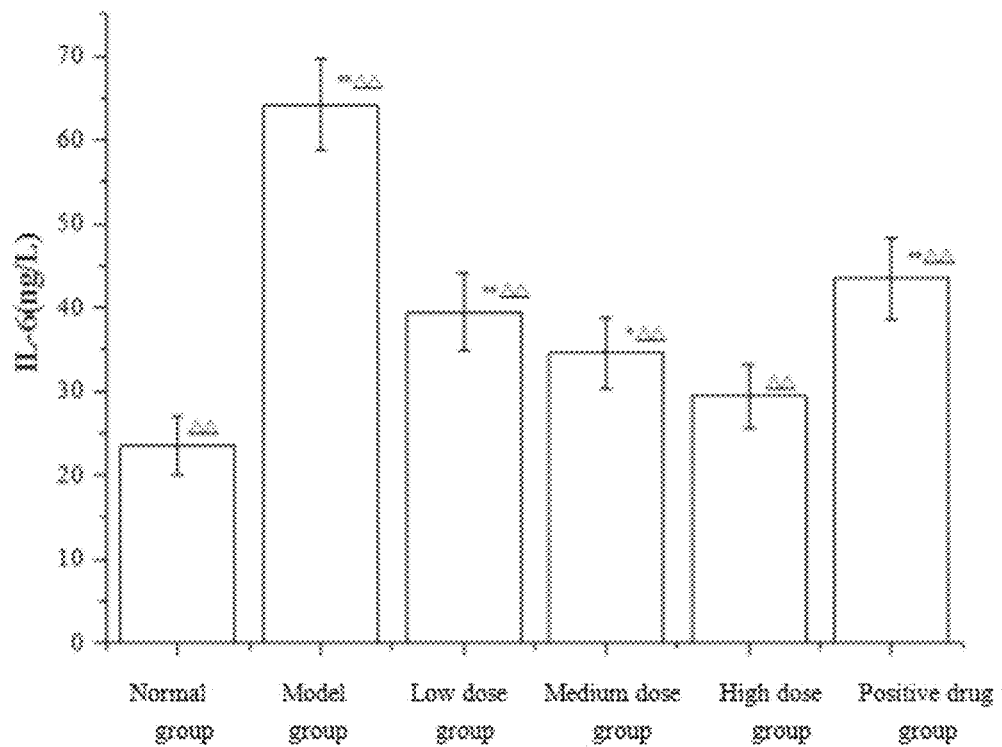
FIG. 9A and FIG. 9B show serum levels of IL-6 and TNF-α in Embodiment 1.
Figure 9B:
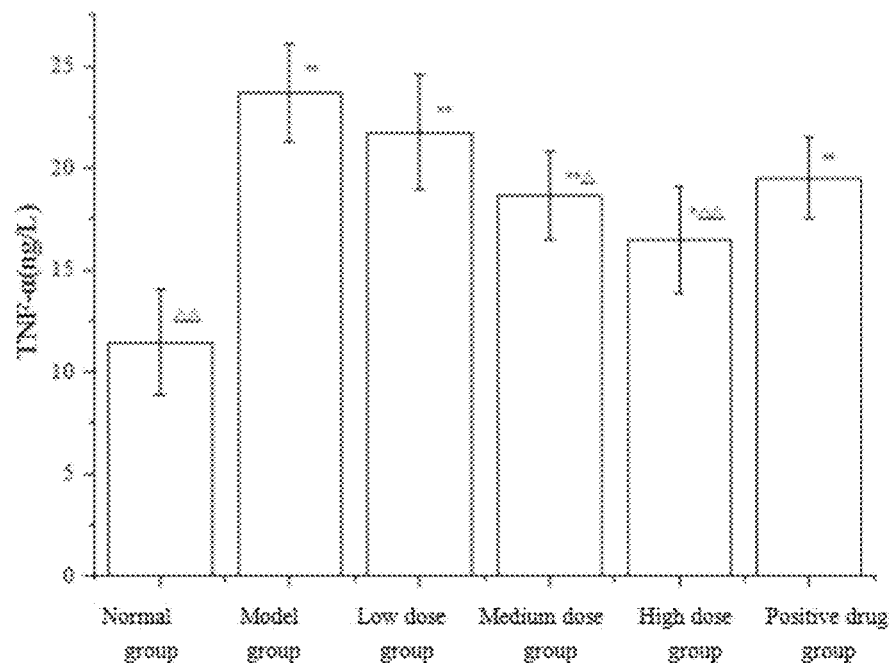

The contents of IL-6 and TNF-α in serum of mice are shown in FIG. 9. From FIG. 9, it can be seen that the contents of IL-6 and TNF-α in serum of mice with tumor cachexia in the model group are obviously increased, while the contents of IL-6 and TNF-α in the intervention group and the positive drug group are obviously decreased compared with the model group, which indicates that the intervention of administration of polysaccharide from citrine pleurotus may obviously improve the inflammatory reaction caused by cachexia.

5.4 Detecting Protein Expression in Muscle Tissue by Western Blot 5.4.1 Cell Treatment and Total Protein Extraction Culturing L6 cells in 6-well plates. After overnight cell adhesion, grouping and treating the cells as shown in TBL 3. After washing the cells with PBS for 2-3 times, adding appropriate RIPA lysis buffer into the culture plate, standing

TABLE 2

| | Muscle fiber quantity | Total muscle fiber area | Single muscle fiber area | Muscle fiber density |
|---|---|---|---|---|
| Normal group | 172 ± 16$^{\Delta\Delta}$ | 0.1757 ± 0.0254 | 0.0010 ± 0.0001$^{\Delta\Delta}$ | 638.701 ± 58.556$^{\Delta\Delta}$ |
| Model group | 92 ± 7** | 0.1628 ± 0.0037 | 0.0017 ± 0.0001** | 341.631 ± 27.287** |
| Low dose polysaccharide group | 1126 ± 1**$^{\Delta\Delta}$ | 0.1857 ± 0.0063 | 0.0014 ± 0.00006**$^{\Delta\Delta}$ | 463.123 ± 35.531**$^{\Delta\Delta}$ |
| Medium dose polysaccharide group | 147 ± 3*$^{\Delta\Delta}$ | 0.1803 ± 0.0248 | 0.0012 ± 0.0001*$^{\Delta\Delta}$ | 544.628 ± 10.647*$^{\Delta\Delta}$ |
| High dose polysaccharide group | 233 ± 10**$^{\Delta\Delta}$ | 0.2174 ± 0.0071**$^{\Delta\Delta}$ | 0.0009 ± 0.000008$^{\Delta\Delta}$ | 863.979 ± 35.531**$^{\Delta\Delta}$ |

Notes:
*$P < 0.05$, **$P < 0.01$ compared with the normal group; compared with the model goup, $^{\Delta}P < 0.05$, $^{\Delta\Delta}P < 0.01$.

From FIG. 8 and TABLE 2, it can be known that after intervention with citrine pleurotus polysaccharide, the transverse diameter of muscle fiber cells increases significantly, the intercellular substance becomes smaller, and the muscle degradation caused by cachexia is improved in a dose-dependent manner. The positive control group also improves muscle fiber, but the effect is significantly less than that of polysaccharide intervention group. Combined with TBL 2, it may be more clearly found that the number of muscle fibers in the intervention group of citrine pleurotus polysaccharide and positive drug is higher than that in the model group, and the number of muscle fibers in the high dose group of polysaccharide is even higher. From the total muscle fiber area and muscle fiber density, it may be found that the administration has a beneficial effect on muscle condition.

5.3 Detection of Serum Indicators

Determining Interleukin IL-6 and Tumor Necrosis Factor TNF-α in mouse serum samples by double antibody sandwich method using Jingmei kit. The standards are diluted according to the instructions. Adding 50 μL of different concentrations of standards to the standard wells of the enzyme plate, 40 μL of sample diluent and 10 μL of sample to be measured in the sample wells, and shaking gently.

at low temperature for 3-5 min, scraping the cells, collecting the cells into a 1.5 mL centrifuge tube, and standing at 4° C. for 2 h to ensure complete lysis of the cells. 12000 rpm, centrifugating at 4° C. for 10 min, and collecting the supernatant into a new centrifuge tube, which is the total protein solution. Determining the protein content with BCA kit, normalizing the protein concentration of the sample, cooking the sample at 100° C. for 15 min to denature the protein, repacking the denatured protein and storing the protein in the refrigerator at −20° C. for standby.

5.4.2 Electrophoresis

Preparing the required concentration of separation gel and 5% concentrated gel according to the experimental requirements, putting the glue maker into the electrophoresis tank, adding enough electrophoresis solution, and then loading the sample for electrophoresis. Adding the sample into the electrophoresis hole, the voltage of concentrated gel is 75V, and the voltage of separated gel is 120V. Electrophoresis may be terminated as soon as bromophenol blue comes out.

5.4.3 Film Transferring

Preparing filter paper and PVDF membrane. PVDF membrane shall be activated with methanol before use. Putting the clamp for membrane transfer, two sponge pads, filter paper and activated PVDF membrane into the box filled with membrane transfer solution. Opening the clip and padding the sponge and three layers of filter paper respectively. Carefully peeling off the separating glue and placing the glue on the filter paper, and covering the PVDF membrane on the glue to avoid bubbles. Turning the film according to a certain voltage and time.

5.4.4 Immune Response

Sealing the improved membrane is sealed with 5% skim milk (0.5% TBST) at room temperature for 1 h and placed on a shaker. After sealing, placing the PVDF membrane in the first antibody diluent (5% skim milk dissolved by TBST, 5% BSA dissolved by TBST for phosphorylated protein), gently shaking by shaking table, and incubating at 4° C. overnight. After taking out PVDF membrane, wash the membrane three times with TBST at room temperature for 5 minutes each time. After washing for 5 ming, placing the PVDF membrane in the second antibody diluent (diluted 3000 times with TBST), incubating for 30 minutes at room temperature, and washing three times with TBST at room temperature for 5 minutes each time.

5.4.5 Chemiluminescence

After the second incubation, taking out the PVDF membrane, mixing ECLA and ECLB reagents with equal volume in a centrifugal tube in a dark room, sticking double gloves or other transparent films on the exposure box, placing the PVDF membrane protein side up between the two films in the exposure box, adding the mixed ECL solution to fully react, after 1-2 min, removing the residual liquid, and covering the upper film to start exposure. The exposed film is developed and fixed with developing and fixing reagents. Adjusting the exposure conditions according to different luminous intensities.

5.4.6 Gel Image Analysis

Figure 10:
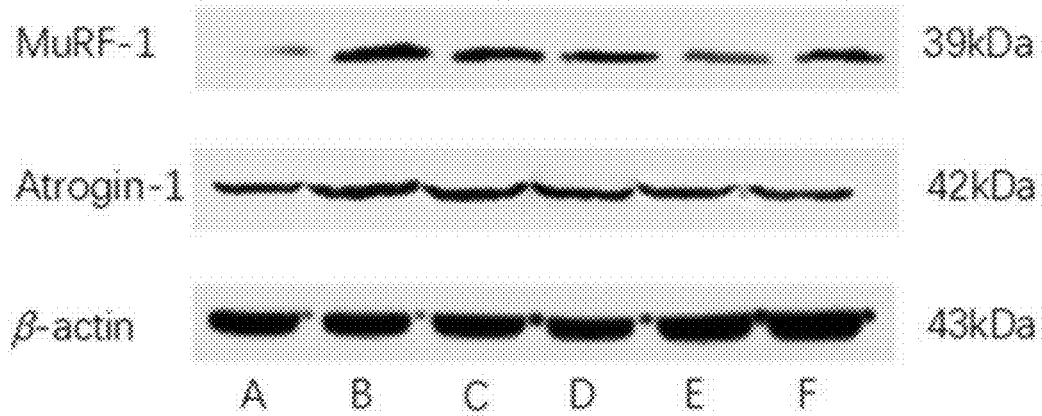
FIG. 10 illustrates protein blots of Atrogin-1 and MuRF-1 in Embodiment 1.

Scanning and archiving the film, and using Alpha software processing system to analyze the optical density value of the target band. Western blotting of Atrogin-1 and Murf-1 is shown in FIG. 10, Atrogin-1 and MuRF-1.

The protein expression is shown in TABLE 3:

TABLE 3

| Group | MuRF-1/β-action | Atrogin-1/β-action |
| --- | --- | --- |
| Normal group | 0.07 | 0.27 |
| Model group | 0.47 | 0.51 |
| Low dose group | 0.37 | 0.44 |
| Medium dose group | 0.33 | 0.37 |
| High dose group | 0.22 | 0.35 |
| Positive drug group | 0.30 | 0.34 |

From FIG. 10 and TABLE 3, it can be seen that the polysaccharide of citrine pleurotus prepared in Embodiment 1 can down-regulate the protein expression of Atrogin-1 and MuRF-1, the marker genes of muscle reduction cancer.

5.5 Using Real-Time PCR to Detect the mRNA Expression in Muscle Tissue.

5.5.1 Extraction of Total RNA from Tissues

Extracting total RNA (miRNA) in gastrocnemius muscle by guanidine isothiocyanate-phenol-chloroform extraction method. Accurately weighing 100 mg of tissue and lysing the tissue with 1 mL of TRIzol reagent. Adding 0.2 mL chloroform, shaking vigorously, standing at room temperature for 3 min, then centrifuging at 4° C. with 12,000 g for 15 min, and RNA is dissolved in the upper water phase. Transferring the upper water phase to a 1.5 mL centrifuge tube, adding isopropanol according to the amount of 0.5 mL isopropanol per 1 mL TRIzol, standing at room temperature for 10 min, centrifuging at 4° C. with 12,000 g for 10 minutes, removing the supernatant, and there will be white RNA at the bottom. Adding 75% ethanol prepared by RNase-free water, vortex mixing for 20 s, and centrifuging at 7,500 g for 5 min Removing the supernatant, standing in the air for 5-10 min, adding 20 μL of RNase-free water, water bathing at 60° C. for 15 min for reverse transcription or storing at −70° C.

5.5.2 cDNA Synthesis of cDNA

In a 0.2 mL Ep tube, preparing the reaction solution according to the instructions of ABI reverse transcription kit. The specific operation is shown in TABLE 4-1.

TABLE 4-1

| Operating steps of RNA extraction | |
| --- | --- |
| Buffer solution | 4 μL |
| Reverse transcrptase (200 U/μL) | 1 μL |
| Oligo dT primer | 1 μL |
| 10 mM template | 2 μL |
| RNA enzyme inhibitor (20 U/μL) | 1 μL |
| Total RNA | 1000 ng |
| Rnase free water | up to 20 μL |

5.5.3 Design and Synthesis of Primers

Comparing the sequences of the reported genes on GenBank, and designing primers for the above genes using Primer 5.0 and other related biology software for subsequent experiments, and the designed primer sequences are shown in TABLE 4-2.

TABLE 4-2

| Design and Synthesis of Gene Primers | | | | |
| --- | --- | --- | --- | --- |
| Gene name | Gene ID | Primer location | Primer sequence | Amplification length |
| FBXO32 | 114907 | F | SEQ ID NO: 1 | 244 |
| | | R | SEQ ID NO: 2 | |
| TRIM63 | 84676 | F | SEQ ID NO: 3 | 101 |
| | | R | SEQ ID NO: 4 | |
| β-actin | 11461 | F | SEQ ID NO: 5 | 245 |
| | | R | SEQ ID NO: 6 | |

5.5.4 Real-Time PCR

The cDNA obtained from the above reverse transcription is subjected to q-PCR reaction to detect the gene expression level. The reaction system is shown in TABLE 4-3.

TABLE 4-3

| q-PCR reaction system | |
| --- | --- |
| Reagent | Dosage |
| Ultrapure water | 5.2 μL |
| 2xSYBR Mix | 10 μL |
| Forward primer (10 μM) | 0.4 μL |
| Reverse primer (10 μM) | 0.4 μL |
| Template | 4 μL |
| General system | 20 μL |
| 90° C., 30 s | 40 cycles |
| | 95° C., 15 s, 60° C., 30 s |

The expression levels of target genes Atrogin-1, MuRF-1 and internal reference gene β-actin (beta-actin) in cells are detected, and the ΔΔCt values are obtained according to the qPCR reaction curve, which is used for relative quantification.

Figure 11:
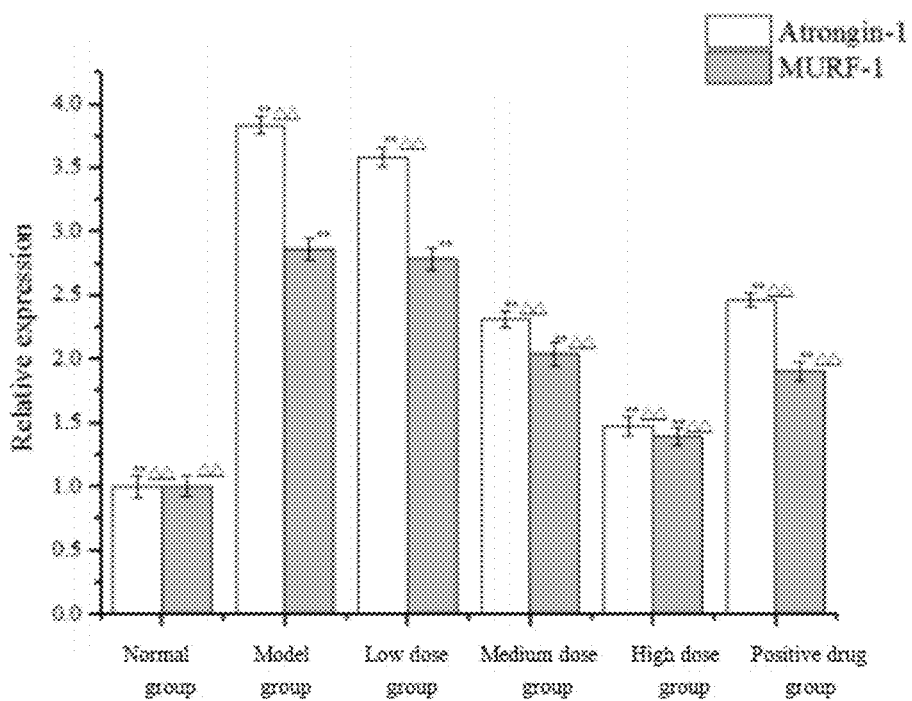
FIG. 11 shows mRNA expressions of Atrogin-1 and MuRF-1 in Embodiment 1.

The mRNA expression levels of Atrogin-1 and MuRF-1 are shown in FIG. 11. From FIG. 11, it can be seen that citrine pleurotus polysaccharide prepared in Embodiment 1 can down-regulate the mRNA expression of Atrogin-1 and MuRF-1, the marker genes of sarcopenia.

To sum up, *Pleurotus citrinopileatus* polysaccharide can alleviate the symptoms of sarcopenia caused by colon cancer.

Test Embodiment 2

The citrine pleurotus polysaccharide prepared in Embodiment 1 is used to verify the muscle attenuation effect of mice with colorectal cancer cachexia. The test process is the same as that of Test Embodiment 1, except that the tumor cell used is colorectal cancer cell CT-26. The results show that citrine pleurotus polysaccharide prepared in this example may alleviate the symptoms of muscle reduction caused by colorectal cancer.

Test Embodiment 3

The effect of citrine pleurotus polysaccharide prepared in Embodiment 2 on muscle attenuation in mice with liver cancer cachexia is verified. The test process is the same as that in Embodiment 1, except that the tumor cells used are liver cancer cells H22. The results show that citrine pleurotus polysaccharide prepared in this example may alleviate the symptoms of muscle reduction caused by liver cancer.

Test Embodiment 4

The same detection as that of Test Embodiment 1 shows that the polysaccharide of citrine pleurotus prepared in Embodiment 2 is composed of xylose, glucose, galactose, glucuronic acid, fucose, fructose and arabinose in the molar ratio of 59.938:26.485:7.234:5.172:0.665:0.396:0.125.

Test Embodiment 5

The effect of citrine pleurotus polysaccharide prepared in Embodiment 2 on muscle attenuation in mice with gastric cancer cachexia is verified. The test process is the same as that in Test Embodiment 1, except that the tumor cells used are gastric cancer cells MFC. The results show that citrine pleurotus polysaccharide prepared in Embodiment 2 may alleviate the symptoms of muscle reduction caused by gastric cancer.

Test Embodiment 6

The effect of citrine pleurotus polysaccharide prepared in Embodiment 2 on muscle attenuation in mice with esophageal cancer cachexia is verified. The test process is the same as that in Test Embodiment 1, except that the tumor cells used are esophageal cancer cells AKR. The results show that *Pleurotus citrinopileatus* polysaccharide prepared in Embodiment 2 may alleviate the symptoms of muscle reduction caused by esophageal cancer.

Test Embodiment 7

The effect of citrine pleurotus polysaccharide prepared in Embodiment 2 on muscle attenuation in mice with cachexia of lung cancer is verified. The test process is the same as that in Test Embodiment 1, except that the tumor cells used are lung cells lewis. The results show that citrine pleurotus polysaccharide prepared in Embodiment 2 may alleviate the symptoms of muscle reduction caused by lung cancer.

Test Embodiment 8

The effect of citrine pleurotus polysaccharide prepared in Embodiment 2 on muscle attenuation in mice with pancreatic cancer cachexia is verified. The test process is the same as that in Embodiment 1, except that the tumor cells used are pancreatic cells PANC02. The results show that citrine pleurotus polysaccharide prepared in Embodiment 2 may alleviate the symptoms of muscle reduction caused by pancreatic cancer.

Test Embodiment 9

The effect of citrine pleurotus polysaccharide prepared in Embodiment 2 on muscle attenuation in mice with lymphoma cachexia is verified. The test process is the same as that in Test Embodiment 1, except that the tumor cell used is lymphoma cell EL4. The results show that citrine pleurotus polysaccharide prepared in Embodiment 2 may alleviate the symptoms of muscle reduction caused by lymphoma.

Test Embodiment 10

The effect of citrine pleurotus polysaccharide prepared in Embodiment 3 on muscle attenuation in mice with lymphoma cachexia is verified. The test process is the same as that in Example 1, except that the tumor cell used is breast cancer cell 4T1. The results show that citrine pleurotus polysaccharide prepared in Embodiment 2 may alleviate the symptoms of muscle reduction caused by breast cancer.

Test Embodiment 11

The citrine pleurotus polysaccharide prepared in Embodiment 3 is tested in the same way as in Embodiment 1. The results show that the citrine pleurotus polysaccharide prepared in Embodiment 3 is composed of xylose, glucose, galactose, glucuronic acid, fucose, fructose and arabinose in the molar ratio of 56.410:29.059:9.235:3.464:0.915:0.644:0.157.

The above-mentioned embodiments only describe the preferred mode of the present disclosure, and do not limit the scope of the present disclosure. Without departing from the design spirit of the present disclosure, all kinds of modifications and improvements made by ordinary technicians in the field to the technical schemes of the present disclosure should fall within the protection scope determined by the appended claims of the present disclosure.

What is claimed is:

1. A medicine for treating sarcopenia in a subject comprising a mixture of polysaccharide compounds from citrine pleurotus (*Pleurotus citrinopileatus*); xylose accounts for more than 50% in molar percentage of the citrine pleurotus polysaccharides, glucose accounts for more than 15% in molar percentage of the citrine pleurotus polysaccharides, galactose accounts for more than 4% in molar percentage of the citrine pleurotus polysaccharides, glucuronic acid accounts for more than 1% in molar percentage of the citrine pleurotus polysaccharides, each of the fucose, fructose and arabinose accounts for less than 3% in molar percentage of the citrine pleurotus polysaccharides along with medically acceptable excipients.

2. A method of preparing the medicine for treating sarcopenia of claim 1, the method comprising combining the mixture of polysaccharide compounds from citrine pleurotus with medically acceptable excipients.

* * * * *

SEQUENCE LISTING

<160> NUMBER OF SEQ ID NOS: 6

<210> SEQ ID NO 1
<211> LENGTH: 19

```
<212> TYPE: DNA
<213> ORGANISM: Artificial Sequence
<220> FEATURE:
<223> OTHER INFORMATION: Primer-F with PrimerBankID 13385848a1 for Gene
      FBXO32

<400> SEQUENCE: 1
cagcttcgtg agcgacctc                                                        19

<210> SEQ ID NO 2
<211> LENGTH: 20
<212> TYPE: DNA
<213> ORGANISM: Artificial Sequence
<220> FEATURE:
<223> OTHER INFORMATION: Primer-R with PrimerBankID 13385848a1 for Gene
      FBXO32

<400> SEQUENCE: 2
ggcagtcgag aagtccagtc                                                       20

<210> SEQ ID NO 3
<211> LENGTH: 21
<212> TYPE: DNA
<213> ORGANISM: Artificial Sequence
<220> FEATURE:
<223> OTHER INFORMATION: Primer-F with PrimerBankID 21523717a1 for Gene
      TRIM63

<400> SEQUENCE: 3
gtgtgaggtg cctacttgct c                                                     21

<210> SEQ ID NO 4
<211> LENGTH: 21
<212> TYPE: DNA
<213> ORGANISM: Artificial Sequence
<220> FEATURE:
<223> OTHER INFORMATION: Primer-R with PrimerBankID 21523717a1 for Gene
      TRIM63

<400> SEQUENCE: 4
gctcagtctt ctgtccttgg a                                                     21

<210> SEQ ID NO 5
<211> LENGTH: 22
<212> TYPE: DNA
<213> ORGANISM: Artificial Sequence
<220> FEATURE:
<223> OTHER INFORMATION: Primer-F with PrimerBankID 145966868c1 for Gene
      beta-actin

<400> SEQUENCE: 5
gtgacgttga catccgtaaa ga                                                    22

<210> SEQ ID NO 6
<211> LENGTH: 19
<212> TYPE: DNA
<213> ORGANISM: Artificial Sequence
<220> FEATURE:
<223> OTHER INFORMATION: Primer-R with PrimerBankID 145966868c1 for Gene
      beta-actin

<400> SEQUENCE: 6
gccggactca tcgtactcc                                                        19
```